United States Patent
Gaffney

[11] Patent Number: 5,864,047
[45] Date of Patent: Jan. 26, 1999

[54] PROPYLENE OXIDE PROCESS USING ALKALINE EARTH METAL COMPOUND-SUPPORTED SILVER CATALYSTS CONTAINING RHENIUM AND POTASSIUM PROMOTERS

[75] Inventor: Anne M. Gaffney, West Chester, Pa.

[73] Assignee: Arco Chemical Technology, L.P., Greenville, Del.

[21] Appl. No.: 827,738

[22] Filed: Apr. 10, 1997

[51] Int. Cl.[6] .................................................. C07D 301/10
[52] U.S. Cl. .............................................................. 549/536
[58] Field of Search .............................. 549/536; 502/397

[56] References Cited

U.S. PATENT DOCUMENTS

| | | | |
|---|---|---|---|
| 4,761,394 | 8/1988 | Lauritzen | 502/348 |
| 4,808,738 | 2/1989 | Lauritzen | 549/536 |
| 4,820,675 | 4/1989 | Lauritzen | 502/216 |
| 4,833,261 | 5/1989 | Lauritzen | 549/536 |
| 4,874,879 | 10/1989 | Lauritzen | 549/536 |
| 5,145,824 | 9/1992 | Buffum et al. | 502/216 |
| 5,364,826 | 11/1994 | Kemp | 502/315 |
| 5,380,885 | 1/1995 | Kemp | 549/536 |
| 5,387,751 | 2/1995 | Hayden et al. | 549/534 |
| 5,447,897 | 9/1995 | Kemp | 502/303 |
| 5,486,628 | 1/1996 | Kemp | 549/536 |
| 5,545,603 | 8/1996 | Kemp | 502/347 |
| 5,597,773 | 1/1997 | Evans et al. | 502/348 |
| 5,625,084 | 4/1997 | Pitchai et al. | 549/536 |
| 5,703,254 | 12/1997 | Gaffney et al. | 549/536 |

FOREIGN PATENT DOCUMENTS

| | | |
|---|---|---|
| 1282772 | 4/1991 | Canada . |
| 1286687 | 7/1991 | Canada . |
| 1286688 | 7/1991 | Canada . |
| 1286689 | 7/1991 | Canada . |
| 0266015 | 5/1988 | European Pat. Off. . |
| 2 495 958 | 6/1982 | France . |
| 9613493 | 5/1996 | WIPO . |

OTHER PUBLICATIONS

International Search Report dated 12 Jun. 1998.

*Primary Examiner*—Ba K. Trinh
*Attorney, Agent, or Firm*—Stephen D. Harper

[57] ABSTRACT

Direct oxidation of propylene to propylene oxide is accomplished using alkaline earth metal compound-supported silver catalysts containing a rhenium promoter and a potassium promoter derived from a potassium salt.

18 Claims, No Drawings

5,864,047

PROPYLENE OXIDE PROCESS USING ALKALINE EARTH METAL COMPOUND-SUPPORTED SILVER CATALYSTS CONTAINING RHENIUM AND POTASSIUM PROMOTERS

FIELD OF THE INVENTION

This invention relates to a process for the direct oxidation of propylene to propylene oxide in the vapor phase using molecular oxygen. In particular, the invention pertains to the use of compositions comprised of silver supported on certain alkaline earth metal-containing compounds to selectively catalyze the formation of epoxides. The performance of the catalysts is improved by incorporating a Re promoter together with a potassium promoter derived from a potassium salt comprising potassium cation and an anion selected from carbon oxyanions and nitrogen oxyanions or precursors thereof.

BACKGROUND OF THE INVENTION

The direct oxidation of ethylene to ethylene oxide by molecular oxygen is well-known and is, in fact, the method used currently for commercial production of ethylene oxide. The typical catalyst for such purpose contains metallic or ionic silver, optionally modified with various promoters and activators. Most such catalysts contain a porous, inert support or carrier such as alpha alumina upon which the silver and promoters are deposited. A review of the direct oxidation of ethylene in the presence of supported silver catalysts is provided by Sachtler et al. in Catalyst Reviews: Science and Engineering, 23 (1&2), 127–149 (1981).

It is also well-known, however, that the catalysts and reaction conditions which are best suited for ethylene oxide production do not give comparable results in the direct oxidation of higher olefins such as propylene. The discovery of processes capable of providing propylene oxide by vapor phase direct oxidation in higher yields than are presently attainable thus would be most desirable.

The use of supported silver catalysts containing relatively low levels of alkali metal promoters and rhenium promoters for direct oxidation of ethylene to ethylene oxide has previously been proposed. For example, U.S. Pat. No. 4,833,261 teaches supported silver catalysts containing a maximum of 3000 ppm alkali metal and 1860 ppm rhenium. The support, according to the patent, is preferably of aluminous composition; the use of an alkaline earth metal carbonate or titanate as a support is not suggested. The alkali metal promoter may be introduced using any of a large number of alkali metal compounds; the choice of counter anion to the alkali metal was apparently not regarded as critical. The patent also discloses that diluents such as carbon dioxide and moderating agents such as dichloroethane may be introduced in the feedstream contacted with the catalyst. The use of a nitrogen oxide species such as NO is not taught, however. Moreover, there is no suggestion in the patent that these catalysts or reaction conditions could successfully be modified or adapted in order to selectively convert propylene to propylene oxide.

SUMMARY OF THE INVENTION

A process for propylene epoxidation is provided wherein a feedstream comprising propylene and oxygen is contacted with a particular type of silver catalyst. The catalyst is comprised of (a) a support; (b) a catalytically effective amount of metallic silver; (c) a promoting amount of a rhenium promoter, and (d) a promoting amount of a potassium promoter. The support is comprised of an alkaline earth metal compound selected from the group consisting of alkaline earth metal carbonates (e.g., calcium carbonate), alkaline earth metal titanates, and mixtures thereof. The rhenium promoter may be derived from a rhenium compound such as an ammonium rhenate. The potassium promoter is derived from a potassium salt such as potassium carbonate which comprises potassium cation and an anion selected from the group consisting of nitrogen oxyanions, carbon oxyanions, and precursors and mixtures thereof.

In one especially advantageous embodiment of the invention, the feedstream additionally comprises a nitrogen oxide species, an organic halide, and, optionally, carbon dioxide.

The process described herein is capable of producing propylene oxide at remarkably high selectivity and productivity as compared to other direct propylene oxidation processes previously known in the art.

DETAILED DESCRIPTION OF THE INVENTION

The present invention is directed to a process for the vapor phase oxidation of propylene to propylene oxide, i.e., an epoxidation process performed in the presence of an oxygen-containing gas and a particular class of supported silver catalysts.

The support material used in the present invention is an alkaline earth metal compound selected from alkaline earth metal carbonates, alkaline earth metal titanates, and mixtures thereof. Carbonates suitable for use include inorganic carbonates having a cation which is an alkaline earth metal ion, particularly calcium, strontium, magnesium or barium, with calcium carbonate being most preferred. Alkaline earth metal carbonate supports are described, for example, in Canadian Pat. No. 1,282,772. Alkaline earth metal titanates comprise the class of inorganic substances containing an alkaline earth metal such as barium, strontium, calcium, or magnesium and a titanate species. Suitable alkaline earth metal titanates thus may correspond to the empirical formula $MTiO_3$, $M_2TiO_4$, and $MTi_2O_5$ wherein M preferably=Ba, Sr, Ca, or Mg. Any of the conventional methods for preparing such substances may be utilized. Barium titanate, for example, may be prepared by heating a mixture of the correct proportions of barium carbonate and titanium dioxide at 1300° C. until the reaction is complete. Strontium titanate may be obtained in pure form by calcining the double strontium titanium oxalate precipitate from titanium tetrachloride solution. The calcium titanate can correspond to the compound $CaTiO_3$ (CAS 12049-50-2), which occurs naturally as the mineral perovskite, but which can also be synthesized by heating equimolar amounts of the oxide to 1350° C. The term "calcium titanate" as used herein also embraces the substances having the formula $3CaO\bullet2TiO_2$ (CAS 12013-80-8) and $3CaO\bullet TiO$ (CAS 12013-70-6). Magnesium titanates include the metatitanate $MgTiO_3$, the orthotitanate $Mg_2TiO_4$, and the dititanate $MgTi_2O_5$.

Such support materials are capable of providing exceptionally high propylene oxide selectivities and have been found to be surprisingly superior to other support materials in this respect. The carriers of the present invention may exist in various forms. In one embodiment, the carrier is one in which the alkaline earth metal compound is the predominate (i.e., at least 50% by weight) or, preferably, substantially the exclusive component of the support (i.e., the support consists essentially of one or more alkaline earth metal compounds). In other embodiments of the invention, the inorganic support material is used in conjunction with a solid substrate, i.e., a subsupport or substructure composed of a more conventional support material, such as alumina (preferably, alpha-alumina). However, the alkaline earth metal compound support material will normally comprise at least 25 weight percent (in most embodiments, at least 35 weight percent) of the finished catalyst.

A granular form of the alkaline earth metal compound support material is preferred in the present invention, particularly when used as the exclusive or predominant component of the support. Alkaline earth metal compound materials suitable for use in the present invention may be commercially obtained as powders which can be converted to the preferred granular form by conventional methods. As described in greater detail below, the granular support may then be impregnated, or coated, with a solution containing a silver compound which is thereafter reduced to elemental (metallic) silver.

Alternatively, as described below, the powdered granular support material may be combined with an appropriate silver compound-containing solution, such as that used conventionally to impregnate solid supports to form a slurry or paste. This material may then be spread on a suitable surface and dried and calcined at an appropriate temperature, such as about 500° C. This results in an alkaline earth metal compound support with silver being supported thereon in its elemental state. The catalyst may then be impregnated with solutions of the rhenium compound and potassium salt serving as sources of the rhenium and potassium promoters described in more detail hereafter, if so desired, and thereafter dried. As an alternative, the rhenium compound and potassium salt may be dissolved in the same silver-containing impregnation solution used to form the coating paste or slurry with the alkaline earth metal compound material. The rhenium compound and the potassium salt may also be introduced at different steps of the catalyst preparation.

The support material, before or after incorporation of the silver, potassium salt and rhenium compound, can be formed into shaped composites suitable for use in propylene oxide manufacture. The composites may be formed by any suitable technique. For instance, it is possible to form the composites by compressing the support materials into a mold having a desired configuration. The size of the particles may be selected to be appropriate for the formation of the composite and are often in the range of about 0.001 to about 5 millimeters in major dimension.

When coated catalysts, i.e., those catalysts in which the alkaline earth metal compound material is coated on a substructure are employed, a slurry of said material, in either powder or granular form, may be mixed with the particles of substructure support material and thereafter dried. As with the predominant or exclusive alkaline earth metal compound support materials described above, the coated catalysts may also be prepared by using a solution of a silver compound, rhenium compound, and potassium salt or separate solutions of silver compound, rhenium compound and potassium salt to form the slurry, followed by suitable drying and calcination.

The surface area of the alkaline earth metal compound support material generally is at least 0.6 $m^2/g$, preferably at least 1.5 $m^2/g$. However, alkaline earth metal compound support materials having relatively high surface areas (e.g., 50 to 100 $m^2/g$) are also effective for the purposes of this invention. This result was surprising in view of the preference generally expressed in the direct olefin oxidation field for low surface area supports (typically, 0.03 to 10 $m^2/g$). The surface area is measured by the conventional B. E. T. method using nitrogen or krypton described by Brunauer, Emmett and Teller in J. Am. Chem. Soc. 60, 309–16 (1938).

The support materials used in the present invention may generally be described as porous or microporous and typically have water pore volumes of about 0.05 to 0.80 cc/g.

The supported silver catalysts are typically used as individual particles of irregular shape and size. This is true both for the predominate or exclusive alkaline earth metal compound supports as well as the alkaline earth metal compound-coated supports. However, in some instances the supports, particularly the coated supports, may have a particular shape and size and this is especially true of the subsupports used with the alkaline earth metal compound. Typically the subsupports are formed into aggregates or "pills" of a size and configuration to be usable in tubular reactors. These pills may be formed by conventional extrusion and firing techniques. The pills generally range in size from about 2 mm to about 15 mm, preferably about 3 mm to about 12 mm. The size is chosen to be consistent with the type of reactor employed. For example, in fixed bed reactor applications, sizes ranging from about 3 mm to about 10 mm have been found to be most suitable in the tubular reactors commonly utilized. The shapes of the carrier aggregates useful for purposes of the present invention can vary widely and can be any of the forms conventionally used in the heterogeneous catalyst art.

The alkaline earth metal compound- and alkaline earth metal compound-coated supports may be prepared as indicated above or obtained commercially. The supported catalyst of the present invention may be prepared by any known method of introducing silver and/or a promoter in soluble form to a support. A preferred method of introducing silver to the alkaline earth metal compound support is by an impregnation process in which a solution of a silver compound (which can be a salt or complex of silver) in an amount sufficient to deposit the desired weight of silver upon the support is dissolved in a suitable solvent or "complexing/solubilizing" agent. The solution may be used to impregnate the support by immersing the support in the silver compound-containing impregnating solution and forming a pasty mixture or slurry. The slurry is then dried and calcined by placing the mixture in an oven or furnace at about 100 to about 120° C. for 0.5 to 6 hours and then heating the mixture at a temperature of from about 250° to about 600° C. for another 1 to 6 hours. This procedure accomplishes drying of the alkaline earth metal compound/silver mixture, removes volatile components and reduces the silver present to its elemental form.

The potassium salt and rhenium compound may be introduced to the catalyst, either simultaneously or separately, as impregnation solutions in a separate impregnation step or steps. Again, this may be done by any known manner of impregnating a porous material. Conveniently, this may be carried out by placing the catalyst material in a container, evacuating the container and thereafter introducing the solution(s). Alternatively, the support may be sprayed or sprinkled with the impregnating solution(s). The excess solution may then be allowed to drain off or the solvent may be removed by evaporation under reduced pressure at a suitable temperature. The catalyst may then be dried at a moderate temperature (e.g., at 120° C.) in a oven for one-half to five hours. Such a procedure is known as a "sequential" or "consecutive" method of preparation. The alkaline earth metal compound-supported catalyst may also be prepared by a "simultaneous" or "coincidental" method of preparation. With this method, the potassium promoter and the rhenium compound are included in the silver compound-containing solution used to impregnate the support.

The choice of silver compound used to form the silver-containing impregnating solution in a solvent or a complexing/solubilizing agent is not particularly critical and any silver compound generally known to the art which is both soluble in and does not react with the solvent or complexing/solubilizing agent to form an unwanted product may be employed. Thus, the silver may be introduced to the solvent or complexing/solubilizing agent as an oxide or a salt, such as nitrate, carbonate, or carboxylate, for example, an acetate, propionate, butyrate, oxalate, malonate, malate, maleate, lactate, citrate, phthalate, fatty acid ester, and the like or combinations thereof. In one embodiment, silver (I) oxide is utilized.

A large number of solvents or complexing/solubilizing agents may be suitably used to form the silver compound-containing impregnating solution. Besides adequately dissolving the silver compound or converting it to a soluble form, a suitable solvent or complexing/solubilizing agent should be capable of being readily removed in subsequent steps, either by a washing, volatilizing or oxidation procedure, or the like. The complexing/solubilizing agent, preferably, should also permit solution to provide silver in the finished catalyst to the extent of preferably about 10 to about 60 percent silver, based on the total weight of the catalyst. It is also generally preferred that the solvents or complexing/solubilizing agents be readily miscible with water since aqueous solutions may be conveniently employed. Among the materials found suitable as solvents or complexing/solubilizing agents for the preparation of the silver compound-containing solutions are alcohols, including glycols, such as ethylene glycol, amines (including alkanolamines such as ethanolamine and alkyldiamines such as ethylene-diamine) and carboxylic acids, such as lactic acid and oxalic acid, as well as aqueous mixtures of such materials.

Typically, a silver compound-containing solution is prepared by dissolving a silver compound in a suitable solvent or complexing/solubilizing agent such as, for example, a mixture of water, ethylenediamine, oxalic acid, silver oxide, and monoethanolamine. The solution is then mixed with support particles and drained. Thereafter the particles are suitably dried.

As indicated above, after impregnation, the silver compound-impregnated support particles are treated to convert the silver compound to silver metal and thereby effect deposition of silver on the surface of the support. As used herein, the term "surface", as applied to the support, includes not only the external surfaces of the support but also the internal surfaces, that is, the surfaces defining the pores or internal portion of the support particles. This may be done by treating the impregnated particles with a reducing agent, such as hydrogen or hydrazine and/or by roasting, at an elevated temperature to decompose the silver compound and reduce the silver to its free metallic state. Certain solubilizing agents such as alkanolamines, alkyldiamines, and the like may also function as reducing agents.

Although at least a catalytically effective amount of silver must be present in the finished catalyst (meaning an amount that provides a measurable conversion of propylene to propylene oxide), the silver concentration preferably is from about 2 percent to 70 percent, by weight, based on the total weight of the catalyst. More preferably, the silver concentration ranges from about 10 to 60 percent by weight.

It has been unexpectedly discovered that the presence of potassium in the preparation of the supported silver catalyst significantly enhances the efficiency of said catalyst as a propylene epoxidation catalyst. Surprisingly, other alkali metals such as cesium which are well-known as promoters in the ethylene oxide art fail to improve catalyst performance to an appreciable extent. The potassium is introduced by means of a potassium salt, with the selection of particular anions as counter ions to the potassium cation being found to be critical to the attainment of optimum catalyst performance. The anion may be a carbon oxyanion (i.e., an anion or negative ion which contains both carbon and oxygen atoms) such as carbonate or bicarbonate. Potassium carbonate ($K_2CO_3$) is the preferred potassium salt. A nitrogen oxyanion such as nitrate, nitrite, or other negative ion containing both nitrogen and oxygen atoms may alternatively serve as the anion. Potassium compounds containing species capable of being converted to carbon oxyanions or nitrogen oxyanions under the catalyst preparation or epoxidation conditions (i.e., which are carbon oxyanion or nitrogen oxyanion precursors) are also suitable for use.

The efficiency-enhancing potassium salt may be introduced to the catalyst in any known manner. Thus, impregnation and deposition of silver and the potassium salt may be effected coincidentally or sequentially. For example, the support could be impregnated with a solution or solutions of the rhenium compound, potassium salt and silver compound, dried, and then calcined to reduce the silver compound and generate the active supported silver catalyst.

In order to perform coincidental impregnation, the potassium salt must be soluble in the same solvent or complexing/solubilizing agent used with the silver impregnating solution. With a sequential procedure in which the silver is added first, any solvent capable of dissolving the salt which will neither react with the silver nor leach it from the support is suitable. Aqueous solutions are generally preferred, but organic liquids, such as alcohols, may also be employed. Suitable procedures for effecting introduction of a potassium salt to a solid support are well known in the art.

The potassium salt is used in an amount sufficient to provide a potassium promoter concentration which results in an improvement in one or more of the catalytic properties (e.g., selectivity, activity, conversion, stability, yield) of the supported silver catalyst as compared to a catalyst not containing the potassium promoter. The precise amount will vary depending upon such variables as the composition in the feed stream, the amount of silver contained in the catalyst, the surface area of the support, the process conditions, e.g., space velocity and temperature, and morphology of support. It has been found, however, that a minimum of at least 0.5 percent by weight of the potassium promoter, calculated as cation, based on the total weight of the catalyst must be present for the catalyst to exhibit a significant advantage over an analogous catalyst containing no potassium promoter. Potassium concentrations as high as 10 percent by weight may be utilized, although generally little additional benefit is realized beyond a concentration of 5 weight percent. More preferably, the potassium promoter level is an amount corresponding to about 1 to about 3 weight percent K.

The other necessary component of the alkaline earth metal compound-supported silver catalysts of this invention is a promoting amount of a rhenium promoter. Other metal promoters such as Mo, W, Sn and the like may also be present, but the catalyst is capable of operating at relatively high activity and selectivity even when essentially free of metals other than the required silver and rhenium. "Promoting amount" means an amount that works effectively to provide an improvement in one or more catalytic properties of a catalyst as compared to a catalyst not containing a rhenium promoter. The exact form of the rhenium promoter under epoxidation operating conditions is not known. The rhenium promoter, it is believed, is not present on the catalyst in the elemental form since the promoter is applied to the catalyst in the form of compounds (including ions, salts and/or complexes) and the reducing conditions generally used to reduce the silver to metallic silver are not usually sufficient to reduce the rhenium compounds to the elemental form.

It is thought that the rhenium promoter deposited on the support or present on the catalyst is in the compound form, most probably in the form of an oxygen-containing or oxidic compound. In a presently preferred embodiment, the rhenium promoter is introduced to the catalyst in the oxyanionic form, i.e., in the form of an anion, or negative ion which contains oxygen. Examples of anions of rhenium that can be suitably applied include the perrhenates. The anions can be prepared by the reactive dissolution of various non-anionic rhenium compounds such as the oxides (e.g., $Re_2O_7$) as well as other materials such as acids, carbonates, sulfates, halides, oxyhalides, hydroxyhalides, hydroxides, sulfides, etc., of Re. The cation forming the counter ion to the anion in the rhenium compound is most suitably ammonium, although alkali metal or alkaline earth metal cations may also be utilized.

The carrier is impregnated with rhenium promoter compound(s). This may be done at the same time that the other components of the catalyst are added or before and/or later. In one advantageous and convenient embodiment of the invention, the rhenium compound, potassium salt and silver are incorporated into the catalyst simultaneously.

It has been found that the minimum amount of rhenium promoter present in or deposited on the support or catalyst needed to measurably improve catalyst performance is 0.2 weight percent Re (measured as the element irrespective of the form in which the promoter is present) based on the total weight of the supported silver catalyst. Generally speaking, the maximum amount of rhenium promoter will be 10 weight percent. Operation within the range of 0.2 to 2.5 weight of Re is particularly advantageous.

The degree of benefit obtained within the above-defined limits will vary depending upon particular properties and characteristics, such as, for example, reaction conditions, catalyst preparative techniques, surface area and pore structure and surface chemical properties of the support utilized, silver content of the catalyst, and potassium content of the catalyst.

The presence of the indicated and claimed amounts of rhenium promoter in this specification and claims does not preclude the use of other activators, promoters, enhancers, stabilizers, improvers, and the like.

The rhenium promoter compounds used in the preparation of the instant catalysts are preferably rhenium compounds that can be solubilized in an appropriate solvent. Preferably, the solvent is a water-containing solvent. More preferably the solvent is the same solvent used to deposit the silver compound and potassium salt.

In the epoxidation process of this invention, propylene and an oxygen-containing gas (i.e., a gas comprising molecular oxygen) are brought together in a reactor in the presence of the previously described catalyst under conditions effective to accomplish at least partial oxidation of the propylene to the corresponding epoxide. Typical epoxidation conditions include temperatures within the reaction zone of the reactor on the order of about 180° to 350° C. (more preferably, 200° to 300° C.) and pressures from about 1 to about 60 atmospheres. To favor high selectivity to epoxide, it is desirable that the feed stream contain carbon dioxide and/or an organic halide (described in more detail hereafter). A gaseous nitrogen oxide species (described in more detail hereafter) is also desirably supplied to the reaction zone within the reactor by introducing said species to the feedstream containing propylene (fresh and/or recycled) and molecular oxygen.

Examples of nitrogen oxide species suitable for introduction in the feedstream include at least one of NO, $NO_2$, $N_2O_4$, $N_2O_3$ or any gaseous substance capable of forming one of the aforementioned gases, particularly NO and $NO_2$, under epoxidation conditions, and mixtures of one of the foregoing, particularly NO, with one or more of CO, $PH_3$, $SO_3$ and SO2. NO is the most preferred nitrogen oxide species.

The amount of gaseous nitrogen oxide species present is not critical, although it will be highly advantageous to expose the catalyst to the nitrogen oxide species either prior to use (as a preconditioning step) or while being used in the epoxidation process. The optimum amount is determined, in part, by the particular potassium salt and rhenium compound used and the concentrations thereof, and by other factors noted above which influence the optimum amount of potassium salt and rhenium promoter. Typically, a suitable concentration of the nitrogen oxide species for epoxidation of propylene is about 0.1 to about 2,000 ppm by volume, when $N_2$ is used as a ballast.

The "oxygen" employed in the reaction may be defined as including pure molecular oxygen, atomic oxygen, any transient radical species derived from atomic or molecular oxygen capable of existence under epoxidation conditions, mixtures of another gaseous substance with at least one of the foregoing, and substances capable of forming one of the foregoing under epoxidation conditions. The oxygen is typically introduced to the reactor either as air, commercially pure oxygen or other substance which under epoxidation conditions both exists in a gaseous state and forms molecular oxygen.

The gaseous components which are supplied to the reaction zone, or that region of the reactor where reactants and catalyst are brought together under epoxidation conditions, are generally combined before being introduced to the reactor. If desired, however, such components may alternatively be introduced separately or in various combinations. The feedstream having the particular composition previously described thus may be formed prior to or at the time the individual components thereof enter the reaction zone. The use of the term "feedstream" herein thus is not meant to limit the present process to the embodiment where all of the gaseous components are combined prior to introduction of said components into the reaction zone. The reactors in which the process and catalyst of the present invention are employed may be of any type known to the art. A brief description of several of the reactor parameters which may be used in the present invention is presented below.

In addition to propylene and oxygen, the feedstream also desirably contains a performance-enhancing organic halide such as an alkyl halide. The organic halide is preferably a volatile compound, i.e., a substance which predominantly exists in gaseous form under the temperature and pressure conditions present in the reaction zone. The normal boiling point of the organic halide is most preferably less than about 100° C. at atmospheric pressure. Compounds containing from 1 to 10 carbon atoms are preferred. Most preferably, the alkyl halide is a chloride species. The term alkyl halide includes both saturated and unsaturated halides, such as ethylene dichloride, ethyl chloride, vinyl chloride, methyl chloride and methylene chloride. Preferably, ethyl chloride is employed as the organic halide. Mixtures of different organic halides may be employed. The amount of organic halide employed will vary depending upon a variety of factors, including the concentration of propylene being oxidized, the particular potassium salts and tungsten compounds, the concentration of nitrogen oxide species as well as other factors noted above as influencing the optimum amount of potassium salt and nitrogen oxide species. However, a suitable range of concentration for the organic halide in the oxidation of propylene is typically about 0.1 to about 2,000 ppm, more preferably about 25 to 500 ppm by volume, of the feedstream. In addition, a hydrocarbon, particularly a saturated hydrocarbon, such as methane, propane, or ethane or mixtures thereof, may be included in the feedstream. The feedstream may also contain a ballast or diluent, such as nitrogen, or other inert gas, particularly when air is used as the source of oxygen. Varying amounts of water vapor may also be present.

Carbon dioxide is also highly desirable to include as a component of the feedstream in the epoxidation process of this invention. The presence of carbon dioxide, within certain limits, has been found to provide surprising improvement in the performance of catalysts within the scope of the invention. In particular, selectivity to propylene oxide generally will increase as the carbon dioxide concentration in the feedstream is increased. Desirable enhancements are generally observed using 1 to 60 volume % CO2 in the feedstream, with 5 to 50 volume % CO2 being preferred. In one embodiment, carbon dioxide is used as the ballast gas.

Another unexpected advantage of the catalyst of this invention is that epoxide productivity is not decreased in the presence of carbon dioxide to the same extent as is observed with similar catalysts such as the molybdenum-promoted catalysts described in U.S. Pat. No. 5,625,084. That is, as carbon dioxide is introduced into the feedstream, not only does epoxide selectivity improve but the drop in catalyst activity (as measured by percent conversion) is much less severe. As a result, the quantity of propylene oxide produced per unit volume of catalyst per hour is not nearly as sensitive to carbon dioxide feedstream content.

The components of the feedstream are most suitably present in the amounts shown in the following table:

| Component | Volume in % (or ppm) for Propylene Oxidation |
|---|---|
| propylene | about 2 to about 50% |
| oxygen | about 2 to about 10% |
| organic halide | 0 to about 2,000 ppm, more preferably, about 20 to 500 ppm |
| nitrogen oxide species | 0 to about 2,000 ppm |
| hydrocarbon other than propylene | 0 to about 80% |
| carbon dioxide | 0 to 60%, more preferably 5 to 50% |
| nitrogen or other ballast gas | remainder. |

Although the present invention can be used with any size and type of vapor phase epoxidation reactor, including both fixed bed and fluidized bed reactors known to the art, it is contemplated that the present invention will find most widespread application in standard fixed bed, multi-tubular reactors such as those now in use as ethylene oxide reactors. These generally include wall-cooled as well as adiabatic or non-wall-cooled reactors. Tube lengths may typically range from about 5 to about 60 feet but will frequently be in the range of from about 15 to about 45 feet. The tubes may have internal diameters from about 0.5 to about 2.5 inches and are expected to be typically from about 0.8 to about 1.5 inches. A plurality of tubes packed with catalyst arranged in parallel within a suitable shell may be employed. GHSV generally range from about 500 to about 10,000 hr$^{-1}$. Typically GHSV values range from about 800 to about 3,000 hour$^{-1}$ at pressures from about 1 to about 60 atmospheres, commonly about 1.1 to about 30 atmospheres. Contact times should be sufficient to convert 0.5 to 70%, preferably 5 to 30%, of the propylene.

EXAMPLES

Example 1

This example demonstrates the preparation, for comparative purposes, of a calcium carbonate-supported silver catalyst which does not contain a Re promoter.

Place a 16 oz. wide mouth jar containing a Teflon-coated stir bar on a stir plate. Add 8.40 g ethylene diamine to the jar, followed by 8.34 g distilled water. Mix well, then slowly add 8.42 g oxalic acid and allow to dissolve completely. Slowly add 14.55 g silver (I) oxide and allow to dissolve completely. Add 2.94 g ethanolamine and 0.95 g potassium carbonate and mix well. Add 20.00 g distilled water and 12.32 g calcium carbonate. Add 10 mixing stones, cap the jar and ball mill for four hours, dry at 110° C. for one hour, then calcine at 300° C. for three hours to yield the calcium carbonate-supported silver catalyst.

Example 2

This example demonstrates the preparation of a calcium carbonate-supported silver catalyst in accordance with the invention. The procedure of Example 1 is repeated, except that 0.20 g NH$_4$ReO$_4$ is added following the addition of the potassium carbonate.

Example 3

This example demonstrates the beneficial effect of incorporating the Re promoter to a supported silver catalyst prepared using an alkaline earth metal carbonate support and a potassium salt. The supported silver catalysts obtained in Examples 1 and 2 had the following elemental compositions shown in Table 1 by analysis:

TABLE 1

| Catalyst | Ag, wt % | Re, wt % | K, wt % |
|---|---|---|---|
| Example 1 | 47 | 0 | 1.7 |
| Example 2 | 45 | 0.37 | 1.3 |

The catalytic performance of each of the aforedescribed supported silver catalysts (2 cc, 14–30 mesh) was evaluated in a ½"316 SS tubular reactor at 250° C., 1200 GHSV, and 30 psig using a feedstream comprised of 10 volume percent propylene, 5 volume percent molecular oxygen, 200 ppm NO, 50 ppm ethyl chloride and variable amounts of carbon dioxide (the balance being nitrogen). The reactor effluent was sampled hourly and analyzed by TCD and FID gas chromatography to determine the extent of propylene conversion and selectivity to propylene oxide. The mass balances reached closure within experimental error. Under these conditions, the results shown in Table 2 were obtained.

TABLE 2

| Catalyst | % CO$_2$ in feed | Propylene Conv., % | Propylene Oxide Sel., % | ppm PO | PO Productivity[1] |
|---|---|---|---|---|---|
| Example 1 | 0 | 11 | 32 | 3575 | 0.7 |
| Example 1 | 11.8 | 8 | 42 | 3352 | 0.6 |
| Example 1 | 51.4 | 5 | 52 | 2698 | 0.5 |
| Example 2 | 0 | 14 | 37 | 5335 | 1.0 |
| Example 2 | 11.2 | 10 | 51 | 4928 | 0.9 |
| Example 2 | 52.1 | 7 | 57 | 3978 | 0.7 |

With the Re promoter present, the propylene conversion, PO selectivity and PO productivity improved as compared to the base catalyst (Example 1) containing no metal promoter. This effect was observed whether or not CO2 was present in the feedstream.

We claim:

1. A process for propylene epoxidation comprising contacting a feedstream comprising propylene, oxygen, carbon dioxide, a nitrogen oxide species and an organic halide at a temperature of from 200° C. to 300° C. with a supported silver catalyst comprised of:

(a) a support comprised of calcium carbonate;

(b) a catalytically effective amount of metallic silver;

(c) from 0.2 to 2.5 weight percent Re; and (d) from 0.5 to 5 weight percent K derived from a potassium salt selected from the group consisting of potassium carbonate, potassium bicarbonate, potassium nitrate, potassium nitrite, and mixtures thereof.

2. The process of claim 1 wherein the support consists essentially of calcium carbonate.

3. The process of claim 1 wherein the Re is derived from a rhenium compound having rhenium in oxyanionic form.

4. The process of claim 1 wherein the nitrogen oxide species is NO.

5. The process of claim 1 wherein the potassium salt is potassium carbonate.

6. The process of claim 1 wherein the supported silver catalyst is comprised of 10 to 60 weight percent Ag.

7. The process of claim 1 wherein the calcium carbonate comprises at least 25 weight percent of the supported silver catalyst.

8. The process of claim 1 wherein the supported silver catalyst is obtained by a method comprising impregnating the support with one or more solutions comprising a silver compound, the potassium salt, and a rhenium compound to form an impregnated support and thereafter reducing the silver compound in the impregnated support to metallic silver.

9. The process of claim 8 wherein the rhenium compound is a perrhenate.

10. The process of claim 1 wherein carbon dioxide comprises from 5 to 50 volume percent of the feedstream.

11. The process of claim 1 wherein the organic halide is an organic chloride.

12. The process of claim 1 wherein the supported silver catalyst is comprised of 1 to 3 weight percent K.

13. A process for propylene epoxidation comprising contacting a feedstream comprising propylene, oxygen, carbon dioxide, NO and an organic chloride at a temperature of from 200° C. to 300° C. with a supported silver catalyst comprised of:

(a) a support comprised of at least 50% by weight calcium carbonate;

(b) from 10 to 60 weight percent Ag;

(c) from 0.2 to 2.5 weight percent Re; and (d) from 1 to 3 weight percent K derived from a potassium salt selected from the group consisting of potassium carbonate, potassium bicarbonate, potassium nitrate, potassium nitrite and mixtures thereof.

14. The process of claim 13 wherein the organic chloride is selected from the group consisting of ethylene dichloride, ethyl chloride, vinyl chloride, methyl chloride, and methylene chloride.

15. The process of claim 13 wherein the Re is derived from a rhenium compound having rhenium in oxyanionic form.

16. The process of claim 15 wherein the rhenium compound is ammonium perrhenate.

17. The process of claim 13 wherein the potassium salt is potassium carbonate.

18. The process of claim 13 wherein the supported silver catalyst is obtained by a method comprising impregnating the support with one or more solutions comprising a silver compound, the potassium salt, and a rhenium compound wherein rhenium is in oxyanionic form to form an impregnated support and thereafter reducing the silver compound in the impregnated support to metallic silver.

* * * * *